United States Patent
Rahmer et al.

(10) Patent No.: US 9,770,304 B2
(45) Date of Patent: Sep. 26, 2017

(54) MULTIMODAL FIDUCIAL MARKER AND MARKER ARRANGEMENT

(71) Applicant: KONINKLIJKE PHILIPS N.V., Eindhoven (NL)

(72) Inventors: Jürgen Erwin Rahmer, Hamburg (DE); Bernhard Gleich, Hamburg (DE); Jörn Borgert, Hamburg (DE); Michael Harald Kuhn, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 357 days.

(21) Appl. No.: 14/375,153

(22) PCT Filed: Jan. 22, 2013

(86) PCT No.: PCT/IB2013/050541
§ 371 (c)(1),
(2) Date: Jul. 29, 2014

(87) PCT Pub. No.: WO2013/114247
PCT Pub. Date: Aug. 8, 2013

(65) Prior Publication Data
US 2015/0011861 A1 Jan. 8, 2015

Related U.S. Application Data
(60) Provisional application No. 61/593,402, filed on Feb. 1, 2012.

(51) Int. Cl.
*A61B 19/00* (2006.01)
*A61B 5/05* (2006.01)
(Continued)

(52) U.S. Cl.
CPC ............ *A61B 19/54* (2013.01); *A61B 5/0071* (2013.01); *A61B 5/0515* (2013.01); *A61B 90/39* (2016.02);
(Continued)

(58) Field of Classification Search
CPC .............. A61B 19/54; A61B 2090/392; A61B 2090/3933; A61B 2090/3941;
(Continued)

(56) References Cited

U.S. PATENT DOCUMENTS 6,102,938 A * 8/2000 Evans ........................ A61F 2/07
623/1.35
2002/0173690 A1 * 11/2002 Jahrmarkt ............ A61N 5/1001
600/8
(Continued)

FOREIGN PATENT DOCUMENTS

EP 1769769 A1 4/2007
JP 2009195614 A 9/2009
(Continued)

OTHER PUBLICATIONS

Gleich, B. et al "Tomographic Imaging using the Nonlinear Response of Magnetic Particles" Nature, vol. 435, 2005, pp. 1214-1217.
(Continued)

*Primary Examiner* — Long V Le
*Assistant Examiner* — Katherine McDonald

(57) ABSTRACT

A multimodal fiducial marker for registration of multimodal data, including a first portion comprising magnetic material visible in magnetic particle imaging (MPI) data obtained by a magnetic particle imaging method and a second portion comprising a second material visible in image data obtained by another imaging method, which image data is registrable with the MPI data and a corresponding marker arrangement.

15 Claims, 2 Drawing Sheets

(51) Int. Cl.
*A61B 5/00* (2006.01)
*A61B 90/00* (2016.01)

(52) U.S. Cl.
CPC ............... *A61B 2090/3933* (2016.02); *A61B 2090/3941* (2016.02); *A61B 2090/3954* (2016.02); *A61B 2090/3995* (2016.02); *A61B 2576/00* (2013.01)

(58) Field of Classification Search
CPC .... A61B 2090/3954; A61B 2090/3995; A61B 5/0515
USPC .......................................................... 600/409
See application file for complete search history.

(56) References Cited

U.S. PATENT DOCUMENTS

| | | | |
|---|---|---|---|
| 2003/0085703 A1 | 5/2003 | Gleich | |
| 2004/0167391 A1* | 8/2004 | Solar | A61B 34/20 600/411 |
| 2006/0004286 A1* | 1/2006 | Chang | A61B 5/06 600/435 |
| 2007/0110665 A1* | 5/2007 | Bolan | A61B 19/54 424/1.11 |
| 2007/0148095 A1 | 6/2007 | Chen | |
| 2007/0258888 A1 | 11/2007 | Feldmann | |
| 2008/0021313 A1 | 1/2008 | Eidenschink | |

FOREIGN PATENT DOCUMENTS

| | | |
|---|---|---|
| WO | 2004091386 A2 | 10/2004 |
| WO | 2004091390 A2 | 10/2004 |
| WO | 2004091394 A2 | 10/2004 |
| WO | 2004091395 A2 | 10/2004 |
| WO | 2004091396 A2 | 10/2004 |
| WO | 2004091397 A2 | 10/2004 |
| WO | 2004091398 A2 | 10/2004 |
| WO | 2004091408 A2 | 10/2004 |
| WO | 2005089664 A1 | 9/2005 |
| WO | 2009009760 A1 | 1/2009 |
| WO | 2009136764 A2 | 11/2009 |
| WO | 2009150564 A2 | 12/2009 |
| WO | 2011003902 A2 | 1/2011 |

OTHER PUBLICATIONS

Parra, Nestor Andres "Rigid and Non-Rigid Point-based Medical Image Registration", FIU Electronic Theses and Dissertations, Paper 127, 2009.

Mutic, Sasa et al "Multimodality Image Registration Quality Assurance for Conformal Three-Dimensional Treatment Planning", International Journal of Radiation Oncology, Biology Physics, Sep. 2001, vol. 51, No. 1, pp. 255-260.

Fitzpatrick, Etal "Predicting Error in Rigid-Body Point-Based Registration", IEEE Transactions on Medical Imaging, vol. 17, Issue 5, Oct. 1998.

* cited by examiner

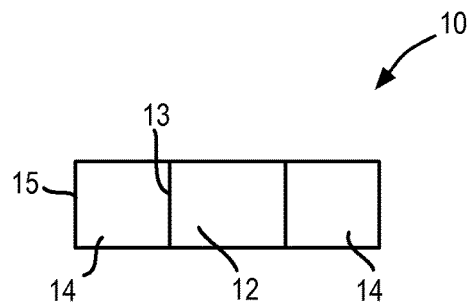
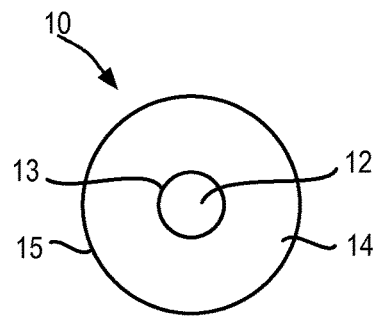
FIG.1A　　　　　　　　FIG.1B
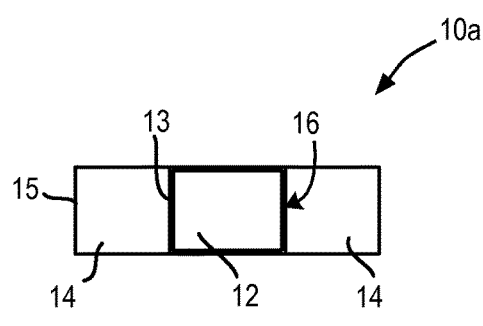
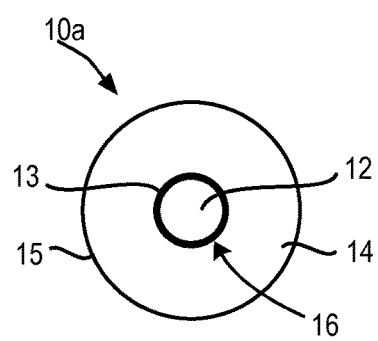
FIG.2A　　　　　　　　FIG.2B
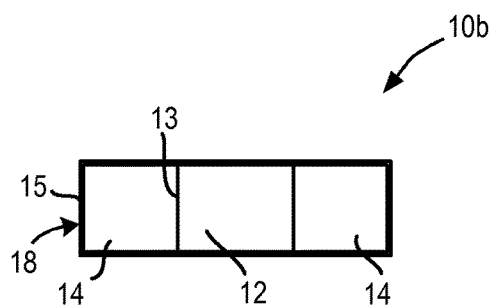
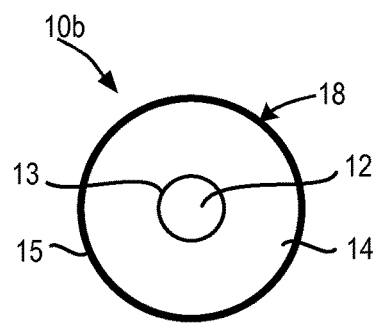
FIG.3A　　　　　　　　FIG.3B

MULTIMODAL FIDUCIAL MARKER AND MARKER ARRANGEMENT

This application is the U.S. National Phase application under 35 U.S.C. §371 of International Application No. PCT/IB2013/050541, filed on Jan. 22, 2013, which claims the benefit of U.S. Provisional Patent Application No. 61/593,402, filed on Feb. 1, 2012. These applications are hereby incorporated by reference herein.

FIELD OF THE INVENTION

The present invention relates to a multimodal fiducial marker for registration of multimodal data and marker arrangement.

BACKGROUND OF THE INVENTION

Multi-modal markers, i.e. markers that can be detected by more than one modality, allow for the registration of images by one modality to images from another modality. Important examples are quantitative images of the distribution of magnetic tracer material, which are obtained by MPI (Magnetic Particle Imaging) and images of the anatomy, which can be obtained by MRI (Magnetic Resonance Imaging). In the case of pre-clinical studies that involve the examination of specimen or for the body part of a patient that is fixed during imaging to avoid movements, the registration of holder devices is also desired, as it can be assumed that the object or specimen is in a fixed relation to the holder device. Thus, the images of the object or specimen are also registered if the holder device is registered, assuming that there is no motion of the specimen or body part with respect to the holder device.

MPI-visible fiducial markers allow robust registration of MPI images to anatomical images obtained using MRI or CT (Computed Tomography), and to other functional data obtained from hybrid PET-CT (PET=Positron Emission Tomography), PET-MR or SPECT-CT (SPECT=Single Photo Emission Computed Tomography) systems, if these markers are also visible in these other modality images.

Image registration between anatomical MRI or CT images, especially pre-clinical images with sub-0.1 mm spatial resolution, and MPI images—with their comparably low spatial resolution in the mm range—can be difficult when based on anatomical landmarks, because anatomical landmarks cannot easily and accurately be automatically detected in the respective modalities. Fiducial markers for this purpose should be easily detectable and localizable in the modality images, preferably with very high (sub-pixel (for 2D) or sub-voxel (for 3D)) accuracy.

SUMMARY OF THE INVENTION

It is an object of the present invention to provide a multimodal fiducial marker for registration of multimodal data that minimizes adverse effects of the properties of the fiducial markers relevant for one modality on any of the respective other modalities, in particular in terms of image distortion or any other form of image degradation.

It is a further object of the present invention to provide a marker arrangement that can be used for automated registration of multimodal data.

In a first aspect of the present invention a multimodal fiducial marker is presented comprising a first portion comprising magnetic material visible in MPI data obtained by a magnetic particle imaging method and a second portion comprising a second material visible in image data obtained by another imaging method, which image data shall be registered with said MPI data.

Hence, according to the present invention, the same fiducial markers can be used for obtaining the MPI data (which are generally also image data, i.e. can also be called MPI image data) by use of an MPI method and the image data by use of one or multiple other imaging methods. The first portion and the second portion are configured, or additional means are provided, such that the first portion does not adversely affect the other imaging method and its image data and that the second portion does not adversely affect the MPI method and the MPI data. The proposed fiducial marker is thus detectable by different imaging modalities and is then visible in the data obtained by these different imaging modalities.

According to a preferred embodiment said first portion is provided in a first compartment and said second portion is provided in a second compartment, said first compartment being located inside the second compartment. In that way the outer compartment can be used to shield the magnetic particles within the inner compartment in order not to disturb the outer magnetic field that shall be measured, e.g. in MR imaging.

Further, said first compartment and said second compartment are configured as concentric spheres or ellipsoids. This embodiment is simple to manufacture and avoids the generation of direction-dependent distortions (e.g. as potentially generated by other forms, in particular non-rotational symmetric forms, of compartments.

Preferably, the diameter ratio of diameter of the first compartment to the diameter of the second compartment is in the range from 1:1 to 1:10, in particular in the range from 1:3 to 1:7. Generally, the diameter ratio is inversely proportional to the cubic root of the field strength of the magnetic field used for obtaining the image data (e.g. MRI data).

In an embodiment the multimodal fiducial marker further comprises a third portion arranged between the first portion and the second portion or within the second portion. This third portion thus separates the first and second portions to avoid mutual adverse affects. Preferably, said third portion is configured as a diamagnetic shell separating the first portion from the second portion. It is thus achieved that the outer magnetic field of the marker is zero, i.e. the paramagnetism of the magnetic material of the first portion is cancelled.

Further, said third portion is preferably made from a diamagnetic material, in particular bismuth or graphite. The use of bismuth would allow the marker to be easily localized in an energy-resolved Computer Tomography imaging system, using k-edge imaging principles.

In an embodiment the multimodal fiducial marker further comprises an outer reflective coating. The marker is thus visible for optical measurements for optical imaging or for position detections or navigation systems.

In another embodiment the multimodal fiducial marker further comprises fluorescent material to the second portion or an outer coating of the marker. This further allows localization of the marker in optical fluorescence imaging.

Preferably, said magnetic material comprises soft magnetic metal or magnetic particles dissolved in a solution or integrated into soft plastics. The integration into soft plastics provides a long-term stability of the magnetic material.

The second material preferably comprises one or more of water, oil, radiopaque material, radioactive material, iodine, gadolinium, gold, bismuth, rubber, or substances containing other MR-active isotopes including one or more of $^{19}F$, $^{13}C$, or $^{23}Na$, mainly depending on the kind of imaging method used for obtaining the imaging data. Said imaging methods may include one or more of MRI, CT, PET, SPECT or any other imaging method.

Multimodal fiducial markers, as proposed according to the present invention and as described above, can be detected in different modalities, allowing for the registration and fusion of image information from both modalities, e.g. the anatomical information from MRI and the distribution of a magnetic tracer material obtained with MPI. The marker-based registration, however, is a process that is currently been performed manually. Furthermore, the markers are generally fixed to the object or specimen under examination. These markers take valuable user time to attach, can slip, fall off and thus registration can become erroneous and unreliable.

Hence, in a further aspect of the present invention a marker arrangement is presented that can be placed on a subject from which multimodal data shall be acquired, comprising a plurality of multimodal fiducial markers as proposed according to the present invention for registration of the acquired multimodal data and a holder holding said plurality of multimodal fiducial markers. For use said holder may be rigidly attached to the subject, but is generally removable from the subject.

Preferably, said multimodal fiducial markers are arranged as a chiral marker arrangement. Such a chiral marker arrangement provides that the mapping between the images of the markers in the two modalities is unique.

In preferred embodiments, the marker arrangement comprises one or more individual sub-markers, wherein the correlation of one sub-marker allows the registration up to a translation and the correlation more than one sub-marker subsequently reduces the number of undefined degrees of freedom. For instance, six markers allow for the determination of an affine transformation which includes scaling, 3D rotation and translation. However, other numbers of markers are also possible.

One or more sub-marker can be specially marked, e.g. by concentric rings or triangles in contrast to singular discs, to allow for the distinction from the rest, simplifying the correlation and registration process.

Several different marker arrangements are chiral and can be used. In a preferred embodiment said multimodal fiducial markers are arranged resembling a letter, e.g. the letter P. Said chiral marker arrangement is preferably arranged on the surface of a transparent plastic tube with cylindrical or elliptic cross-section, as they are commonly used with pre-clinical imaging cells.

Still further, in an embodiment one or more multimodal fiducial markers of said plurality of multimodal fiducial markers are configured to be distinguishable from the other multimodal fiducial markers of said plurality of multimodal fiducial markers, in particular have different forms, materials and/or sizes, thus simplifying the correlation and registration process.

BRIEF DESCRIPTION OF THE DRAWINGS

These and other aspects of the invention will be apparent from and elucidated with reference to the embodiment(s) described hereinafter. In the following drawings FIG. 1 shows a first embodiment of a multimodal fiducial marker according to the present invention, FIG. 2 shows a second embodiment of a multimodal fiducial marker according to the present invention, FIG. 3 shows a third embodiment of a multimodal fiducial marker according to the present invention.

DETAILED DESCRIPTION OF THE INVENTION

Figure 4:
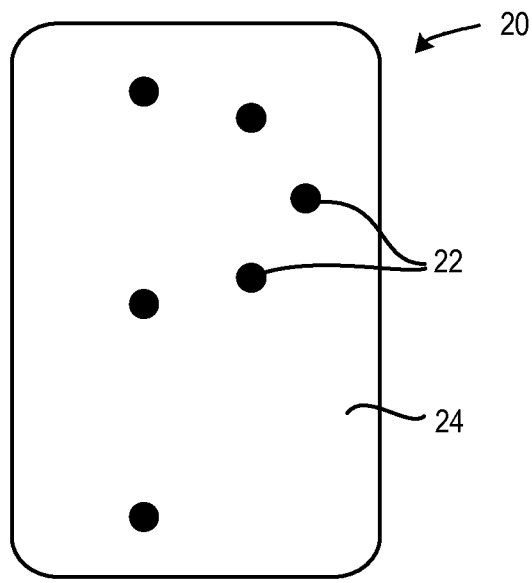
FIG. 4 shows an embodiment of a chiral marker arrangement according to the present invention.

Magnetic Particle Imaging (MPI) is an emerging medical imaging modality. The first versions of MPI were two-dimensional in that they produced two-dimensional images. Newer versions are three-dimensional (3D). A four-dimensional image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MPI image of an object's volume of interest is generated in two steps. The first step, referred to as data acquisition, is performed using an MPI scanner. The MPI scanner has means to generate a static magnetic gradient field, called the "selection field", which has a (single) field-free point (FFP) or a field-free line (FFL) at the isocenter of the scanner. Moreover, this FFP (or the FFL; mentioning "FFP" in the following shall generally be understood as meaning FFP or FFL) is surrounded by a first sub-zone with a low magnetic field strength, which is in turn surrounded by a second sub-zone with a higher magnetic field strength. In addition, the scanner has means to generate a time-dependent, spatially nearly homogeneous magnetic field. Actually, this field is obtained by superposing a rapidly changing field with a small amplitude, called the "drive field", and a slowly varying field with a large amplitude, called the "focus field". By adding the time-dependent drive and focus fields to the static selection field, the FFP may be moved along a predetermined FFP trajectory throughout a "volume of scanning" surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles or other magnetic non-linear materials; if the object is an animal or a patient, a contrast agent containing such particles is administered to the animal or patient prior to the scan. During the data acquisition, the MPI scanner moves the FFP along a deliberately chosen trajectory that traces out/covers the volume of scanning, or at least the field of view. The magnetic nanoparticles within the object experience a changing magnetic field and respond by changing their magnetization. The changing magnetization of the nanoparticles induces a time-dependent voltage in each of the receive coils. This voltage is sampled in a receiver associated with the receive coil. The samples output by the receivers are recorded and constitute the acquired data. The parameters that control the details of the data acquisition make up the "scan protocol".

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model can be formulated as an integral operator that acts on the acquired data; the reconstruction algorithm tries to undo, to the extent possible, the action of the model.

Such an MPI apparatus and method have the advantage that they can be used to examine arbitrary examination objects—e. g. human bodies—in a non-destructive manner and with a high spatial resolution, both close to the surface and remote from the surface of the examination object. Such an apparatus and method are generally known and have been first described in DE 101 51 778 A1 and in Gleich, B. and Weizenecker, J. (2005), "Tomographic imaging using the nonlinear response of magnetic particles" in Nature, vol. 435, pp. 1214-1217, in which also the reconstruction principle is generally described. The apparatus and method for magnetic particle imaging described in that publication take advantage of the non-linear magnetization curve of small magnetic particles.

FIG. 1 shows a first embodiment of a multimodal fiducial marker 10 according to the present invention in a side view (FIG. 1A) and a top view (FIG. 1B). Generally, the fiducial marker 10 comprises a first portion 12 comprising magnetic material visible in MPI data obtained by a magnetic particle imaging method and a second portion 14 comprising a second material visible in image data obtained by another imaging method, which image data shall be registered with said MPI data.

In the preferred embodiment shown in FIG. 1 the fiducial marker 10 comprises two compartments 13, 15 configured as concentric spheres (or, in other embodiments, ellipsoids). The inner compartment 13 houses the first portion 12, e.g. is filled with MPI-active magnetic particles in solution (e.g. Resovist®). The outer compartment 15 houses the second portion 14, e.g. filled with water, oil, or other material visible in a desired imaging modality (e.g. MRI or CT). The outer compartment 15 may e.g. also contain MRI-active nuclei other than 1H—preferably not naturally abundant, e.g. 19F.

The proposed arrangement separates the magnetic particles from direct contact with tissue of the subject to be imaged, e.g. from MRI-active tissue, and thus minimizes artifacts in image data obtained by the second imaging modality induced by the magnetic particles of the first portion.

The outer layer of the inner compartment 13 around the first portion 12, e.g. the magnetic particle solution, also keeps the first portion from evaporating through the compartment 13 (e.g. made of plastic or glass to be disposable) and ensures long-term stability.

In practice, magnetic particles commercially available under the trade name Resovist (or similar magnetic particles) may be used, which have a core of magnetic material or are formed as a massive sphere and which have a diameter in the range of nanometers, e.g. 40 or 60 nm.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

FIG. 2 shows a second embodiment of a multimodal fiducial marker 10a according to the present invention in a side view (FIG. 2A) and a top view (FIG. 2B). This embodiment of the fiducial marker 10a comprises a third portion 16 arranged between the first portion 12 and the second portion 14 (or within the second portion 14). Said third portion 16 may be configured, as shown in FIG. 2, as a diamagnetic shell enclosing the MPI-active portion 12 so that its paramagnetism is canceled. The second portion 14 is then arranged around the diamagnetic material of the third portion 16.

The embodiments shown in FIGS. 1A and 2A may alternatively be seen as cross-sectional side views of 2D markers having a disk-like inner compartment 13 and a cylinder-like outer compartment 15, representing other embodiments of the proposed marker. Similarly, the embodiments shown in FIGS. 1B and 2B may alternatively be seen as cross-sectional top views of 3D markers having a sphere-like inner compartment 13 and a spherical shell-like outer compartment 15, representing other embodiments of the proposed marker.

Ideally, all materials should be bio-compatible, such that the markers could remain in the body, once implanted.

The proposed marker, e.g. the arrangement of the marker using two concentric compartments, is preferably designed such that the outer magnetic field of the marker is zero. This is achieved by the combination of an outer diamagnetic material of the third portion 16, which may also be formed as a compartment enclosing the inner compartment 13, with the inner compartment 13 containing the magnetic particles. Thus the outer region of the marker can be visualized without artifacts using another imaging modality, e.g. MRI.

An estimation for an inner sphere 13 containing pure Resovist (500 mM(Fe)/l) and an outer sphere 15 containing water leads to a required diameter ratio of about 1:6 for an applied field strength of 1.5 T. Generally, the diameter ratio is inversely proportional to the cubic root of the magnetic field strength.

Alternatively, a more efficient diamagnetic material that is also RF-transparent is used to reduce the diameter of the marker, e.g. Bismuth (or Graphite). The second portion, e.g. MRI-visible material, is then arranged around the Bismuth layer of the third portion 16.

For CT contrast, the magnetic particles providing the MPI signal can be used, but alternatively materials with high atomic number are provided in the inner or outer shell filling or the container material itself. For contrast generation in spectral CT, making use of k-edge imaging, materials with k-edge energies in the energy range of polychromatic X-ray sources may be used in the second portion 14, such as Iodine, Gadolinium, Gold, or Bismuth.

FIG. 3 shows a third embodiment of a multimodal fiducial marker 10b according to the present invention in a side view (FIG. 3A) and a top view (FIG. 3B). This embodiment of the fiducial marker 10b comprises a reflective coating 18 that makes the marker 10b optically visible, e.g. to a 3D optical positioning system or for automatic localization on optical images such as the ones used in pre-clinical research on mice and/or rats. Further, for optical measurements, fluorescent markers may be added to the second portion 14, (e.g. a layer of MRI-visible material) or the outer coating 18.

The concentrations and volumes of the different materials and compartments, e.g. MPI, MRI, optical, and CT-active layers, are generally well-defined and well-known for calibration purposes.

Further, preferably fiducial markers with different concentrations should be available, so that the signal level can be matched to the signal level obtained from the object of interest. Otherwise, too much signal from the fiducial markers could compromise image contrast or generate artifacts.

In another embodiment the fiducial marker comprise only a single compartment. For instance, a combined MPI/MRI fiducial marker could contain very low concentrations of Resovist, so that it is just visible with MPI, but is also visible to dedicated MRI sequences, e.g. ultrashort TE sequences.

Solid state markers would be beneficial regarding long-term stability. For MRI, rubber could be used in combination with ultrashort TE sequences. For MPI, particles integrated into soft plastic (e.g. meshes) provide long-term stability. Alternatively, soft-magnetic metals (permalloys, μ metals) could be used to generate MPI signal.

Other preferred embodiments of the proposed marker are implantable, e.g. to permanently mark a tumor position, e.g. for radiation therapy.

Adapted MPI sequences could be employed, which interleave local object measurements with local measurements of the fiducial marker(s). Dynamic acquisition of the marker position could be used to feed a motion model, e.g. to follow or compensate breathing motion.

The detected position of the marker could also be used to control the acquisition protocol, e.g. by having the imaging volume follow the marker for an object subjected to (e.g. table) motion.

For detection in PET and SPECT, the fiducial markers could also be equipped with a suitable radiation source, e.g. 22Na (PET) and 99Mo (SPECT).

The marker proposed according to the present invention thus enables the combination of MPI with MRI, CT, optical imaging or another imaging modality for pre-clinical and clinical applications, including combinations with functional images from hybrid PET-CT, PET-MR, and SPECT-CT images.

The present invention further proposes the use of a marker arrangement 20, in particular a chiral marker arrangement, as shown in the projection of at three-dimensional arrangement depicted in FIG. 4 in an embodiment. The marker arrangement 20 can be attached or integrated into the holder device that is routinely used in pre-clinical studies on objects or specimen. In particular, the proposed marker arrangement 20 can be placed on a subject from which multimodal data shall be acquired and comprising a plurality of multimodal fiducial markers 22 as proposed according to the present invention for registration of the acquired multimodal data and a holder 24 holding said plurality of multimodal fiducial markers 22.

Figure 5:
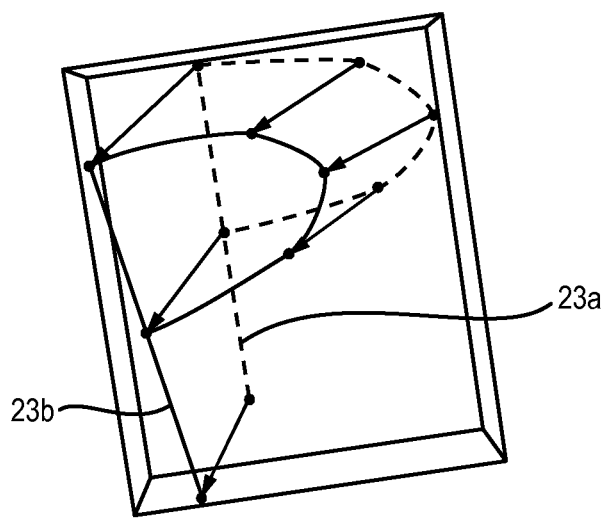
FIG. 5 shows the embodiment of the marker arrangement as shown in FIG. 4 to illustrate that is allows for the determination of an affine transformation.

The marker arrangement 20 comprises one or more individual marker 22, whereas the correlation of one marker allows the registration up to a translation of more than one marker 22 subsequently reduces the number of undefined degrees of freedom. For instance, six markers as provided in the exemplary marker arrangement 20 (the number being not limited to six, but can be less or more) allow for the determination of an affine transformation which includes scaling, 3D rotation and translation as shown in FIG. 5 depicting the six markers in a first position (indicated by 23a) and a second position (indicated by 23b).

By attaching or integrating the markers 22 into the holder 24, the risk of slipping or fall-off is eradicated. By using a chiral marker arrangement 20 as shown as a 2D projection in FIG. 4 the mapping between the images of the marker arrangement 20 in the two modalities is unique.

In an embodiment one or more markers are specially marked, e.g. by concentric rings or triangles in contrast to singular discs, to allow for the distinction from the rest of the markers, simplifying the correlation and registration process.

Algorithms to correlate an arrangement of points in space are generally known in the art, for instance from Parra, Nestor Andres, "Rigid and Non-rigid Point-based Medical Image Registration" (2009), FIU Electronic Theses and Dissertations, Paper 127 currently available at http://digitalcommons.fiu.edu/etd/127 or from Sasa Mutic et al., "Multimodality image registration quality assurance for conformal three-dimensional treatment planning", International Journal of Radiation Oncology*Biology*Physics—1 Sep. 2001 (Vol. 51, Issue 1, Pages 255-260).

It is also known in the art that the registration error increases with increasing distance from the marker assembly (see e.g. Fitzpatrick et al., "Predicting error in rigid-body point-based registration", IEEE Transactions on Medical Imaging, Vol. 17, Issue 5, October 1998). Therefore, the marker arrangement is preferably chosen such that its distribution evenly covers the imaging volume or the volume-of-interest within the imaging volume.

Furthermore, the marker distribution preferably takes into account that different imaging modalities have different imaging volumes, i.e. one modality may "see" markers, which the other modality may not be able to "see". This means that a sufficient number of markers is suitably arranged such that they are located in the imaging volume of all modalities involved.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A multimodal fiducial marker for registration of multimodal data, comprising:
   a first portion comprising magnetic material visible in magnetic particle imaging (MPI) data obtained by a magnetic particle imaging method, the first portion being provided in a first compartment;
   a second portion comprising a second material visible in image data obtained by an imaging method different from the magnetic particle imaging method, the second portion being provided in a second compartment, wherein the first compartment is located inside the second compartment and wherein a diameter ratio of a diameter of the first compartment to a diameter of the second compartment is in the range from 1:1 to 1:10; and
   a third portion arranged between the first portion and the second portion, wherein the third portion is configured as a diamagnetic shell completely surrounding the first portion.

2. The multimodal fiducial marker as claimed in claim 1, wherein the first compartment, the second compartment and the third compartment are configured as concentric spheres or ellipsoids.

3. The multimodal fiducial marker as claimed in claim 1, wherein the diameter ratio of the diameter of the first compartment to the diameter of the second compartment is in the range from 1:3 to 1:7.

4. The multimodal fiducial marker as claimed in claim 3, wherein the third portion is made from bismuth or graphite.

5. The multimodal fiducial marker as claimed in claim 1, further comprising an outer reflective coating.

6. The multimodal fiducial marker as claimed in claim 1, further comprising fluorescent material within the second portion or configured as an outer coating of the multimodal fiducial marker.

7. The multimodal fiducial marker as claimed in claim 1, wherein the magnetic material comprises soft magnetic metal or magnetic particles dissolved in a solution or integrated into soft plastics.

8. The multimodal fiducial marker as claimed in claim 1, wherein the second material comprises one or more of water, oil, radioactive material, iodine, gadolinium, gold, bismuth, rubber, or an MR-active isotope including one or more of $^{19}F$, $^{13}C$, or $^{23}Na$.

9. A marker apparatus, comprising a plurality of multimodal fiducial markers as claimed in claim 1 and a holder holding the plurality of multimodal fiducial markers, wherein the holder is configured for placement on a subject.

10. The marker arrangement as claimed in claim 9, wherein the plurality of multimodal fiducial markers are arranged in a chiral marker arrangement.

11. The marker arrangement as claimed in claim 10, wherein one or more multimodal fiducial markers of the plurality of multimodal fiducial markers are configured to be distinguishable from other multimodal fiducial markers of the plurality of multimodal fiducial markers.

12. The marker arrangement as claimed in claim 11, wherein one or more multimodal fiducial markers of the plurality of multimodal fiducial markers have different forms, materials and/or sizes.

13. The multimodal fiducial marker as claimed in claim 1, wherein the third portion is configured to cancel paramagnetism of the magnetic material of the first portion.

14. The multimodal fiducial marker as claimed in claim 1, wherein the third portion is configured to cancel paramagnetism of the magnetic material of the first portion such that an outer magnetic field produced by the multimodal fiducial marker is zero.

15. A multimodal fiducial marker for registration of multimodal data, comprising:
a first portion comprising magnetic material visible in magnetic particle imaging (MPI) data obtained by a magnetic particle imaging method,
a second portion comprising a second material visible in image data obtained by an imaging method different from the magnetic particle imaging method, and
a third portion arranged between the first portion and the second portion, wherein the third portion is configured as a diamagnetic shell completely surrounding the first portion and separating the first portion from the second portion.

* * * * *